United States Patent [19]

Silverman et al.

[11] Patent Number: 5,205,174

[45] Date of Patent: Apr. 27, 1993

[54] SCAVENGER SUBMERSIBLE VISUAL AND ACOUSTICAL TANK INSPECTION SYSTEM AND METHOD

[76] Inventors: Eugene B. Silverman, 4217 Scarlet Sage Ct., Ellicott City, Md. 21043; Seymour R. Kotler, 1054 St. Margarets Dr., Annapolis, Md. 21401; Harry T. Roman, 25 Laurel Ave., East Orange, N.J. 07017

[21] Appl. No.: 705,687

[22] Filed: May 24, 1991

[51] Int. Cl.⁵ .................... G01N 29/10; G01N 29/24
[52] U.S. Cl. ........................ 73/623; 15/321; 15/339; 376/310; 376/316; 134/167 C; 358/99
[58] Field of Search .............. 15/321, 320, 339, 304; 376/310, 316; 73/601, 620, 623, 627, 628, 629, 644; 358/99; 134/167 C

[56] References Cited

U.S. PATENT DOCUMENTS

| | | | |
|---|---|---|---|
| 4,502,407 | 3/1985 | Stevens | 358/99 |
| 4,530,131 | 7/1985 | Zell et al. | 15/321 |
| 4,578,198 | 3/1986 | Schmidt et al. | 134/167 C |
| 4,763,376 | 8/1988 | Spurlock, Jr.; et al. | 15/104.31 |
| 4,910,823 | 3/1990 | Silverman et al. | 15/1 |
| 5,073,258 | 12/1991 | Boullain, II et al. | 15/321 |

*Primary Examiner*—Herzon E. Williams
*Assistant Examiner*—Rose M. Finley
*Attorney, Agent, or Firm*—Sughrue, Mion, Zinn, Macpeak & Seas

[57] ABSTRACT

The present invention is an apparatus and method of preparing and inspecting a submerged surface of a fluid reservoir. The apparatus includes a chassis sized and shaped to provide an optimally low center of gravity, a propulsion system comprising two independently controllable motor and track means, a scrubbing/vacuuming system disposed at the front of the chassis which includes a scrubbing system designed to mechanically break up sediment on the surface beneath the apparatus and a vacuuming system to remove sediment and sediment-containing fluid from beneath the apparatus, and an inspection system located immediately behind the scrubbing/vacuuming system with respect to the direction of apparatus travel and operative to inspect the freshly cleaned surface with either ultrasonics, optics, or a combination of both.

16 Claims, 9 Drawing Sheets

SCAVENGER SUBMERSIBLE VISUAL AND ACOUSTICAL TANK INSPECTION SYSTEM AND METHOD

BACKGROUND OF THE INVENTION

Field of the Invention

The present invention relates to a method and apparatus for cleaning and inspecting the bottom surfaces of fluid reservoirs, such as storage tanks, pools, sumps, and ponds, without first draining them. More particularly, the invention relates to a remote controlled, submersible vehicle which removes sediment from reservoir surfaces by a scrubbing and/or vacuuming process and simultaneously provides video and/or acoustic inspection of the freshly cleaned surface.

In recent years, environmental and industrial safety concerns have focussed attention on the need to inspect fluid handling facilities for signs of corrosion and structural defects. The use of fluid reservoirs to store fuels, chemicals, waste, and radioactive effluents is common in many industries, particularly the chemical and nuclear power industries. In addition, some fluid reservoirs are involved in the active processing of liquids. These reservoirs are subject to additional stresses since liquids often move through them at elevated temperatures and high velocities. When used for either purpose, the volume and nature of the liquids involved make these reservoirs potential sources of widespread toxic and radioactive contamination. As a result, monitoring their structural integrity is a primary concern of government and industry alike. The consequences of failing to detect structural by the media and in court proceedings before the regulatory agencies.

Inspection of liquid reservoirs is no simple matter since entire systems often must be shutdown to gain access to them. Even where the reservoir is not a part of an active processing system, inspection is impeded by the stored liquid and the inevitable buildup of sediments on the reservoir surfaces. In addition, the suspension of sediment in the fluid itself impedes inspection since these particles reduce visibility and scatter signals which may be used to remotely examine the surfaces. Thus, suspended particles will significantly reduce the resolution of video or acoustic images, limiting the features that can be detected.

The most obvious solution to the difficulties imposed by suspended particles and sediment buildup is to drain and clean the reservoir prior to inspection. However, there are significant problems with this approach. First, operation time is lost as systems which depend upon the reservoir are shut down during the cleaning and inspecting procedure. Second, manpower is tied up by these procedures. Finally, where toxic chemicals or radioactive waste are implicated, personnel are exposed to dangerous conditions. For example, in the nuclear power industry radioactive sediment collects in water filled cooling pools. This water provides shielding against radiation and prevents the escape of radioactive particles. Draining these pools to clean and examine their surfaces removes this shielding, exposing personnel to high radiation levels. In addition, if the sediment dries it is susceptible to wind borne dispersion, increasing the dangers to other on-site personnel and the surrounding communities.

Remote controlled, submersible vehicles have been used in various industries to remove sediment from undrained storage tanks. While the use of these vehicles addresses the dangers and economic costs associated with draining reservoirs for cleaning, the contemporaneous inspection of the reservoir surface for damage or defects is not known to have been practiced. As discussed in connection with the description of the present invention, cleaning and inspection procedures are interrelated and it is more efficient to deal with them concurrently.

Sedimentation is a continuous process, proceeding even as the deposited materials are removed. Thus, fresh sediment will accumulate in the interval between cleaning the surface and inspecting it. Minimizing this interval is one key to obtaining accurate inspection data. On the other hand, the contemporaneous cleaning and inspection of surfaces creates a new problem since scrubbing a surface agitates deposited sediment, thereby increasing the concentration of sediment particles suspended in the liquid. As a result, the scattering problem described earlier may be exacerbated when surface cleaning and inspection are carried out in a one step process.

In addition to the problems created by solid sediments, the suspension of non-miscible liquids creates difficulties in certain storage environments. For example, where oil-based liquids are stored, accumulated moisture may also be present, suspended in the liquid. The consequent inhomogeneity of the liquid leads to the same signal scattering and resolution problems discussed above. The quality and resolution of the images necessary to accurately inspect liquid reservoirs is determined by the size of the features which indicate the presence of structural defects and corrosion. Unfortunately, these features may be as fine as hairline cracks, which are easily obscured by small amounts of sediment or missed in low resolution images. Thus, any image degradation could hinder the timely discovery of structural defects and result in contamination with toxic or radioactive material. Certain features, such as corrosion on the external surface of tanks, grain boundary corrosion, or subtle wear effects, cannot be detected visually under the best of circumstances. In these instances, ultrasonic inspection methods are necessary. Ultrasonic inspection can detect variations in reservoir wall thickness due to corrosion on either the inside or outside wall surface as well as structural defects within the reservoir walls. However, ultrasonic inspection requires the detection of small changes between incident and reflected signals. Consequently, the technique is equally sensitive to the accumulation of sediments on reservoir surfaces and the scattering of signals by suspended particles.

Accordingly, it is a primary object of the present invention to facilitate the cleaning and inspection of a reservoir surface without draining the reservoir of its contents.

It is also an object of the present invention to remove sediment from a reservoir bottom by breaking it up mechanically and vacuuming it away.

It is a further object of the present invention to filter the suspension of sediment and reservoir fluid and return the filtered fluid to the reservoir.

Yet another object of this invention is to minimize the time between surface cleaning and surface inspection, during which sediment can continue to deposit.

A further object of the present invention is to provide a liquid volume free of suspended particles through which optical and ultrasonic inspection signals can pass unscattered.

SUMMARY OF THE INVENTION

In accordance with the foregoing objects, the present invention is a method and apparatus involving a remotely operated, tracked, submersible vehicle comprising a system which mechanically loosens and vacuums deposited sediment from a reservoir surface and an inspection system capable of collecting and transmitting video or ultrasonic images of the freshly cleaned surface. In particular, the present invention utilizes a system to remove reservoir fluid containing suspended sediment from an inspection volume and to supply clean fluid to the inspection volume and, more particularly, a system to continuously remove and filter reservoir fluid having suspended particles from the inspection volume and to supply the inspection volume with reservoir fluid which has been filtered of suspended particles or liquids and thereby minimize the degradation of inspection signals. Furthermore, the present invention utilizes a positioning system to locate the vehicle as it moves across the reservoir surface.

The invention may be operated interactively with an operator following the vehicle motion using the positioning system, a forward looking video camera, or direct observation. Alternatively, the vehicle may operate autonomously by pre-programming an on-board or remote microprocessor.

DETAILED DESCRIPTION OF THE INVENTION

Figure 1:
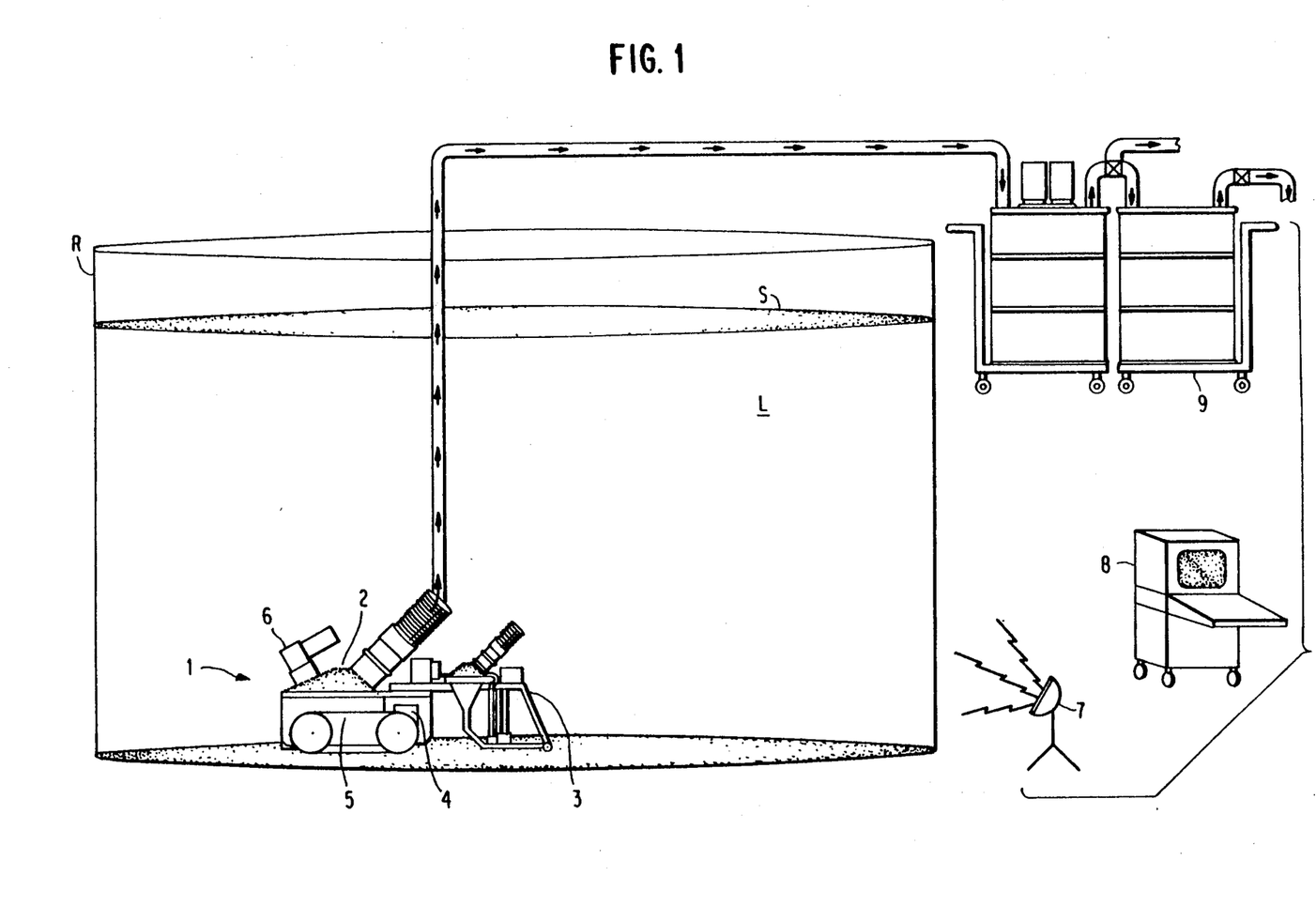
FIG. 1. is a schematic overview showing the cleaning/inspection apparatus of the present invention in a reservoir along with its external remote control, filtering, and positioning systems.

Referring to the drawings, FIG. 1 shows a plan view of a typical liquid reservoir, R, having bottom and side surfaces and filled with liquid, L, that defines a liquid surface, S. Within the reservoir, R, and below the surface, S, is a submersible vehicle 1 having a cleaning system 2, an inspection system 3, a propulsion system 4, including motor driven treads 5, and a navigation system, including a camera 6. Physically connected to or in communication with the vehicle but outside of the reservoir, is positioning system 7, a remote control system 8, and a system for filtering reservoir liquids and returning them to the reservoir 9.

In the preferred embodiment, all vehicle operations are directed from the remote control system 8. Thus, vehicle speed and direction, surface cleaning and inspection, and reservoir fluid processing operations may be regulated from the control system 8. It also receives and processes information from the external positioning system 7, the inspection system 3, and the navigation camera 6. The remote control system can provide video display of all inspection data and, in particular, it can correlate and store information on reservoir surface features as a function of vehicle position. As would be understood by one of ordinary skill in the art, many of these functions need not be performed at the remote control system but could be performed on-board the vehicle, using microprocessors, storage media, and customized programming.

The propulsion system 4 is operative to move the vehicle across the reservoir bottom surface, which may have a variety of accumulated contaminants and may have variations in height and surface orientation. Preferably, the vehicle has a low center of gravity and is made of corrosion and impact resistant materials that can be sealed to contain on-board electronics, motors, actuators, and the like. For example, the body may be constructed of ½" ultra high molecular weight polyethylene (OHWM), 300 series stainless steel, and Delrin. Conventional joint and interface sealing materials may be used.

Figure 2A:
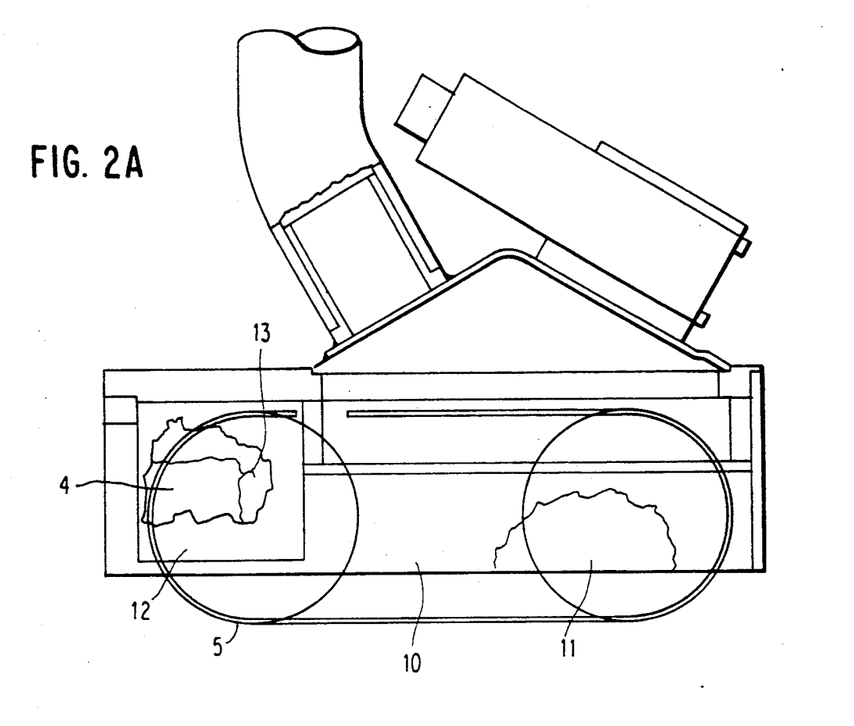
FIG. 2A. is a side view of the robotic vehicle including cutaway views of the sealed motor compartment and the scrubbing/vacuuming compartment.
Figure 2B:
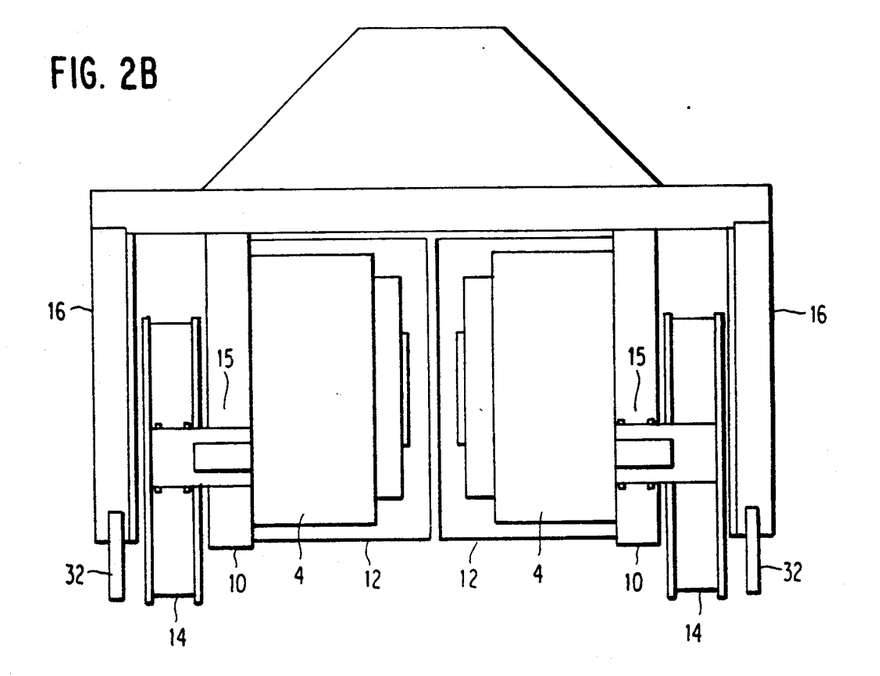
FIG. 2B. is a cutaway view of the motor compartment from the rear of the robotic vehicle, showing the location of the tread motors, drive wheels, and axles.

Referring to FIGS. 2A and 2B, the submersible robotic vehicle is shown having a base chassis 10, a scrubbing/vacuuming compartment 11, and a sealed compartment 12 which houses the propulsion motors 4 and electronics 13. The vehicle chassis 10 is supported on two treads 5 which provide traction for forward and reverse motions, climbing over small surface structures or obstructions, and steering. Preferably, the treads 5 are made of rubber and each is separately driven by a reversible, stall-protected motor 4. The treads are enclosed by an Outer wall 16 which also supports a rubber skirt 32 that extends almost to the surface. The drive wheels 14 for the treads are connected to the two drive motors 4 by sealed axles 15. Because the motors provide a significant part of the vehicle mass, particularly when batteries are not used as the energy source, they are located to provide a low center of gravity to the vehicle. Together, the motors provide adequate thrust to propel the vehicle at speeds sufficient to promote effective cleaning and inspection of the reservoir surface without agitating the sediment. The motors are separately operable in forward and reverse directions, and at various speeds to promote steerability. Ordinarily, vehicle speeds of up to 1 ft/s would be acceptable.

Figure 3:
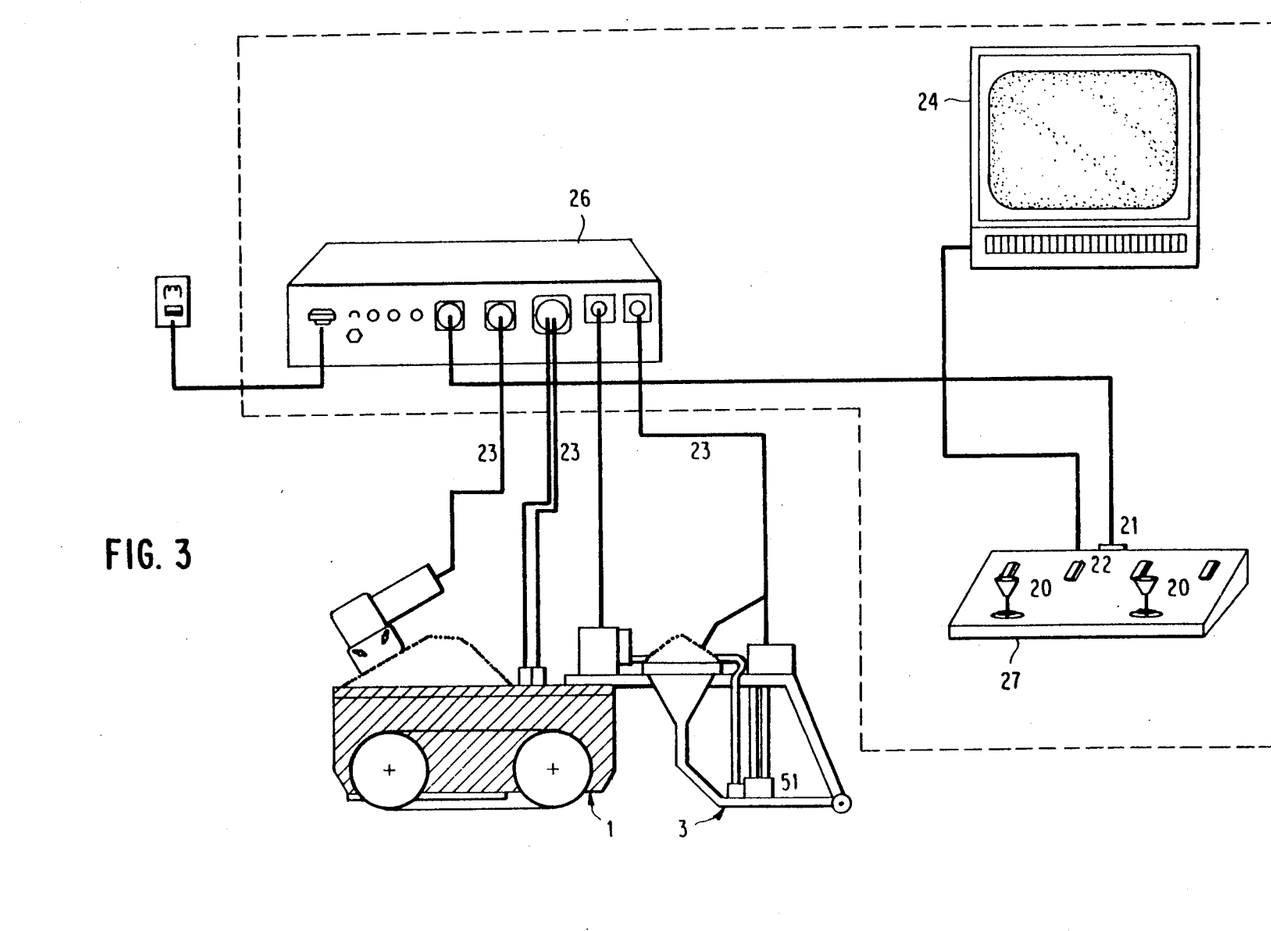
FIG. 3. is a schematic view of the remote control center with connections between user console, power supply, video display, inspection system and robotic vehicle indicated.

FIG. 3 illustrates an embodiment of the remote control system 8. The system is operator controlled via a user console 27 consisting of two joysticks 20, video input and output ports 21 and power switches 22 for the various subsystems. From the console, the operator can maneuver the robotic vehicle, adjust the vehicle speed, regulate the surface scrubbing and vacuuming operations, and activate the inspection system 3. Communication between the control system and the various systems of the robotic vehicle is accomplished by power and control lines 23. Alternatively, when a power/control tether is not desirable, power could be provided by batteries and control could be provided by radio command signals, broadcast from a remotely located transmitter to an on-board receiver. Also, as previously noted, an on-board microprocessor would allow the operator to pre-program certain vehicle functions for automatic operation.

Video signals are provided by navigation camera 6 and optical sensors 52, and time/amplitude signals are provided by ultrasonic transducers 51. These video and amplitude/time signals may be displayed on the video terminal 24. Signals from the forward looking navigation camera 6 provide the operator with a broad, though possibly occluded view of the uncleaned reservoir surface in front of the vehicle, allowing him to adjust the vehicle speed and direction accordingly. Video signals from the optical sensors 52 provide close up views of the freshly scrubbed and vacuumed surface. Finally, signals from the ultrasonic transducers 51 provide the operator with an amplitude/time display which can be analyzed for surface irregularities by conventional techniques. The video and ultrasonic inspection signals may also be stored for later analysis, as discussed below.

In the preferred embodiment, a power supply 26 is connected to the user console 27. It provides 12 V power for the vehicle drive motors 4 and the external pump (not shown) in addition to supplying power for operation of the navigation camera 6 and the inspection system 3, including the CCD camera 53 and the ultrasonic transducers 51.

Figures 4A, 4B:
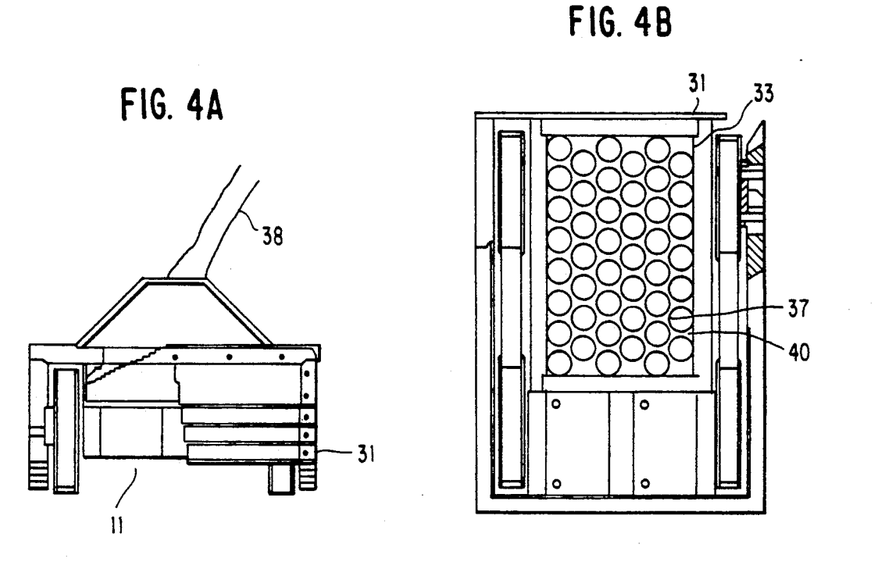
FIG. 4A. is a front view of the robotic vehicle, indicating the location of the scrubbing/vacuuming compartment and front gate.
FIG. 4B. is a bottom view of the robotic vehicle indicating the location of the rotating brush scrubbing mechanism and the vacuum inlet.
Figure 4C:
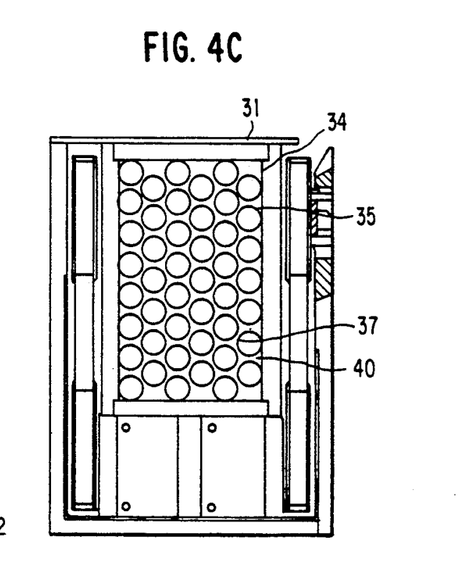
FIG. 4C. is the same as FIG. 4B. with the rotating brush replaced by a hydrolaser scrubbing mechanism.
Figure 4D:
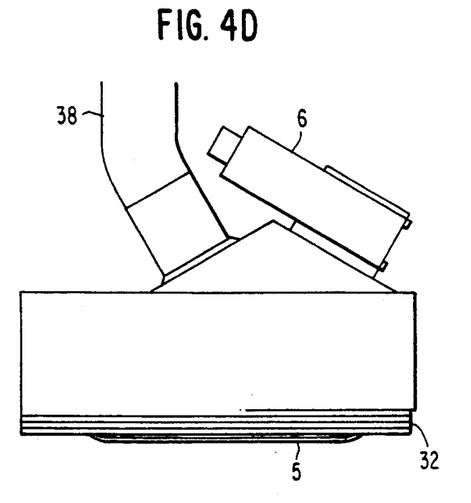

Referring to FIG. 4A, the scrubbing/vacuum compartment 11 is disposed on the front underside of the robotic vehicle 1. The compartment 11 is shown in FIGS. 4B and 4C having a scrubbing mechanism 33, 34 to dislodge sediment from surfaces which may have a variety of irregularities. The sediment is mixed with fluid by the scrubbing action and pumped through a vacuum opening 37 in the top of the scrubbing/vacuuming compartment 11. A flexible pipe 38 transports the fluid/sediment mixture to a filtering system 9 which is located outside the reservoir as indicated in FIG. 1.

A gate 31 at the front of the vehicle, may be adjusted to provide the minimum aperture necessary to accommodate the sludge level in the reservoir. As seen in FIG. 2B, the flexible rubber bottom skirt 32 is located along either side of the vehicle, descending from the outer tread covering 16 almost to the bottom of the vehicle treads 5. The rubber skirt 32 automatically throttles the vacuum and the pressure differential provides additional traction for the robotic vehicle 1. By enclosing the scrubbing/vacuuming operation beneath the robotic vehicle 1, a steady inward movement of fluid is created. This design is effective to prevent movement of dislodged sediment into the fluid surrounding the vehicle 1, thus minimizing any deterioration in visibility.

One embodiment of the scrubbing mechanism, illustrated in the underside view of FIG. 4B, utilizes a rotating brush 33 to break up deposited sediment. The brush may be driven by a geared connection to the propulsion motor 4 or a separate motor may be provided for it. An alternative embodiment of the scrubbing mechanism is the hydrolaser illustrated in FIG. 4C, which utilizes high velocity jets of filtered reservoir fluid to break up deposited sediment. The embodiment shown consists of a manifold of four nozzles 34 mounted to a face plate 34a on the front of the vehicle body 17. The nozzles 34 can be selected to accommodate different spray widths and delivery pressures up to 3000 psi. These would be particularly suitable for highly irregular surfaces. A combination of brushes and hydrolasers, or other dislodging/scrubbing mechanisms may also be used.

The vacuum inlet 37 is located in the top surface of the robotic vehicle and connected by flexible pipe 38 to an external pump (not shown). While a pump may be located on the vehicle 1 within the purview of the present invention, the added weight and vibration that would result may not be desirable. In the preferred embodiment, the pump is capable of moving up to 300 gallons of sediment and fluid per minute through a 2-3" diameter flexible pipe 38 which connects it to the vehicle.

As noted above, turbulence in the reservoir fluid is minimized by arranging the scrubbing mechanism to direct the fluid/sediment suspension into the vacuum inlet 37. The inlet is covered by a screen 40 made of hard, corrosion resistant material. Variable mesh sizes may be used to regulate the sludge flow rate and the maximum size of objects taken into the filter system.

Figure 5A:
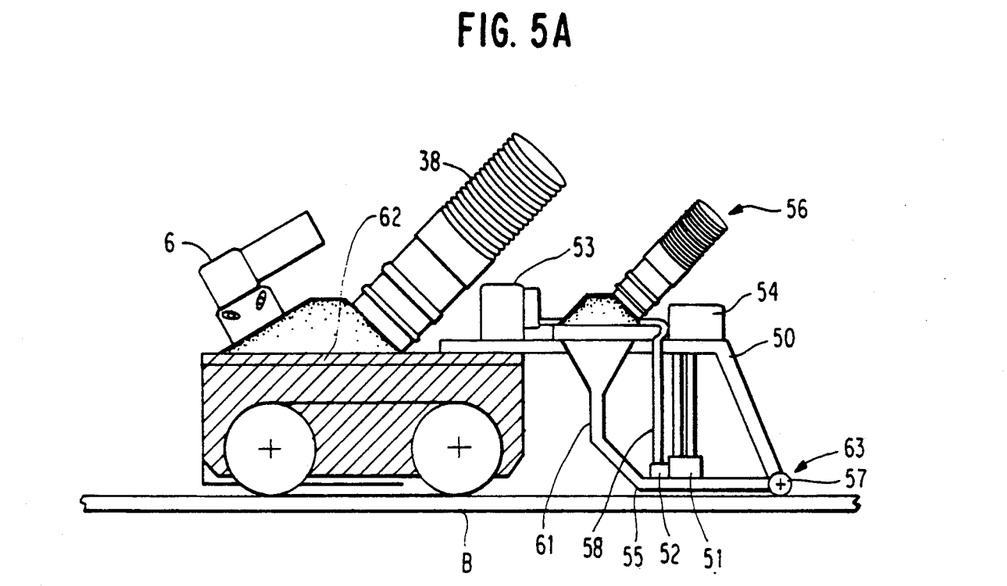
FIG. 5A. is a view of the inspection system, including the optical and ultrasonic inspection systems, the plenum, and the associated electronics.
Figure 5B:
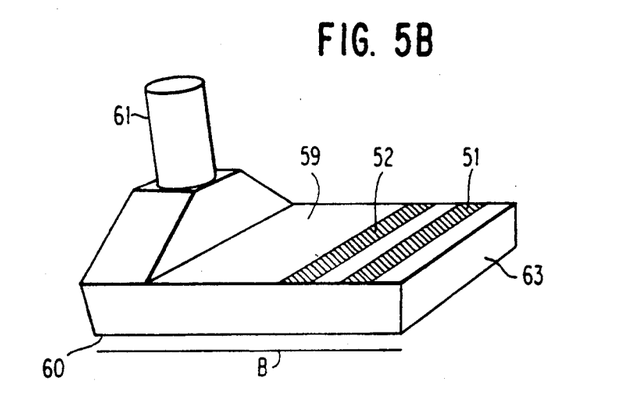
FIG. 5B. is a detailed view of the plenum.

Placement of the inspection system 3, which is illustrated in FIGS. 5A and 5B, is based on the requirement that the interval between surface cleaning and surface inspection be minimized. This may be accomplished by locating the inspection system so that the robotic vehicle's forward motion brings the freshly cleaned surface into the inspection sensor's field of view immediately after the sediment has been removed from it. For example, at a robotic vehicle velocity of 1 ft/s, a sensor array positioned 1 ft. behind the vacuum inlet views a surface that has been scrubbed and vacuumed only one second earlier. Larger separations yield correspondingly longer intervals between surface preparation and inspection. A linear array of sensors with overlapping fields of view, a total width comparable to that of the robotic vehicle, and an orientation perpendicular to the vehicle's direction of motion, allows for cleaning and inspection of the same swath of surface in a single pass.

FIG. 5A illustrates the preferred embodiment of the inspection system 3. A framework 50, provides support for the optical sensors 52, ultrasonic sensors 51, electronics 53, 54, the plenum 55, and plenum fluid supply system 56. The framework 50 is made of lightweight, corrosion resistant material. Attachment to the robotic vehicle 1 may be made by an articulated connection 62, allowing the vehicle to move over uneven terrain. Rollers, skids, or the like 57 may be used to support the rear of the framework 50. The CCD camera, electronics, and light source 53 are mounted on the framework 50, immediately behind the articulated connection 62. Fiber optics 58 transmit the image from the optical sensor lenses 52 to the camera 53. The ultrasonic transducer electronics 54 are located behind the articulated connection 62, directly above the transducer array 51. All electronics are packaged in corrosion-resistant, lightweight materials. The clear fluid supply pipe 56 for the plenum 55 is mounted on top of the framework 50, immediately behind the articulated connection 62. The pipe 56 materials and diameter are selected in accordance with a variety of parameters including the desired flow rate, maximum hydrostatic head which must be overcome, fluid drag per foot of pipe, and the characteristics of the pump. Clear fluid is provided by filtering suspended materials from the contents of the tank.

The plenum 55 is a structure substantially enclosing a volume between the inspection sensors 51, 52 and the bottom reservoir surface B, through which filtered reservoir fluid is continuously passed. The plenum 55 provides a volume in which signal scattering from suspended particles or fluids is minimized. The positive pressure created by the continuous fluid flow prevents unfiltered fluid outside the plenum from entering it and clouding the volume with suspended particles.

In the embodiment illustrated in FIG. 5B, the plenum 55 comprises the volume bounded on top by the surface 59 on which the optical sensors 52 and acoustical sensors 51 are mounted. The plenum sides are bounded by rubber skirts 60 which extend from the surface 59 almost to the reservoir surface B. Fluid enters the volume through an inlet 61 at the forward end and is discharged at the open rear of the volume 63. The fluid is drawn from the contents of the tank, filtered if necessary, and pumped through the plenum 55 at a rate sufficient to provide the volume with steady stream of filtered fluid. For example, a $12''\times 8''\times 2''$ volume would require approximately 50 gallons per minute to flush the 192 in$^3$ space once every second.

The optical inspection system which consists of lenses 52, fiber optics connections 58, a CCD interface 72, and the attendant electronics 53, transmits video images of the surface to the control center video monitor 24 (FIG. 3) for immediate analysis and/or storage for subsequent analysis. The present invention contemplates using an array of lenses arranged to image a section of the surface comparable in width to the swath cleaned by the scrubbing/vacuuming system.

Figure 6A:
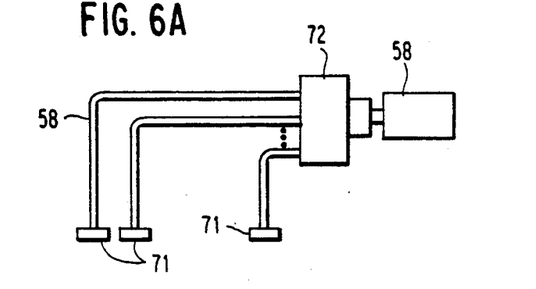
FIGS. 6A and 6B. provide views of one embodiment of the optical inspection system, detailing the fiber optic system connecting the sensor lenses to the CCD camera.
Figure 6B:
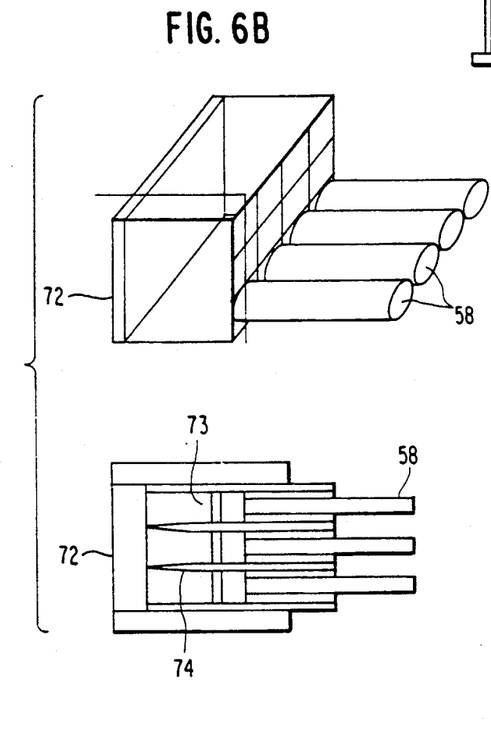

One embodiment of the optical system is illustrated in FIG. 6A. Commercially available fiber optic elements 58 transmit surface images from the sensor lenses 52 to a CCD interface 72. As illustrated in FIG. 6B, a second set of lenses 73 and baffles 74 may be used to focus the individual images onto the CCD 72.

Figure 7A:
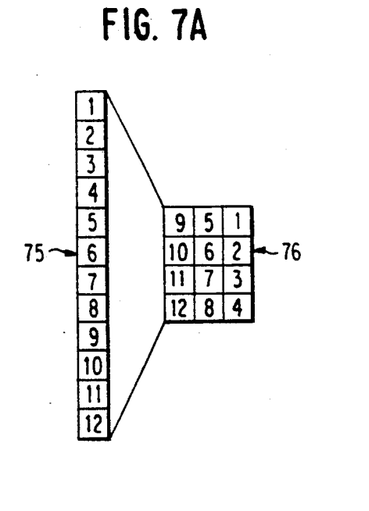
FIGS. 7A and 7B. indicate one way to map the linear sensor array is onto the CCD board.
Figure 7B:
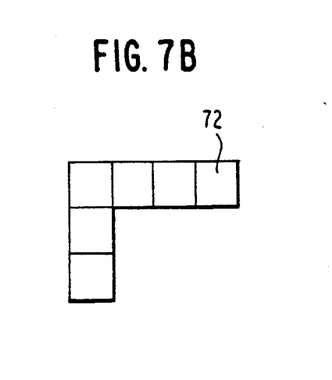

One possible mapping configuration of the sensor images onto the CCD interface 72 is illustrated in FIG. 7A, where a linear array 75 of twelve sensor lenses 52 is mapped onto a $3\times 4$ array of CCD sections 76. As shown in FIG. 7B, a $256\times 256$ pixel CCD board 72 may be subdivided into a $4\times 4$ array of sixteen equal areas. Mapping images from the twelve lenses 52 onto a $3\times 4$ subset of the CCD sections 76 provides each sensor with $64\times 64$ pixel array.

Figure 8A:
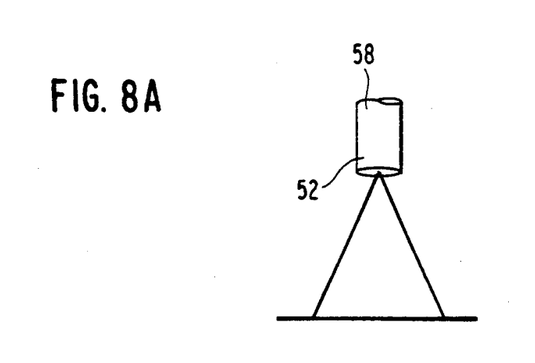
FIGS. 8A and 8B. indicate the orientation and location of the fiber optic/lens elements with respect to the surface and the fields of view of the individual elements.
Figure 8B:
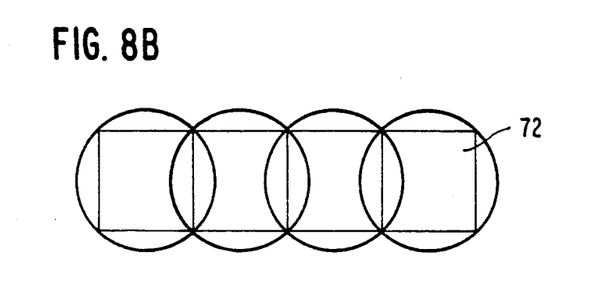

As illustrated in FIG. 8A, the lenses 52 are preferably arranged with their optic axes perpendicular to the surface B to be inspected. In the illustrated configuration, the lenses 52 are preferably located 2" above the surface B, but other lens/surface distances are possible, provided that lens focal lengths are adjusted appropriately. With the lenses 52 spaced at 1" intervals and each lens imaging a 1.5" dia. area, as illustrated in FIG. 8B, images from adjacent lenses overlap with each lens corresponding to a 1 in$^2$ area. This arrangement allows the operator to view a $12''\times 1''$ swath of the surface.

Figure 9:
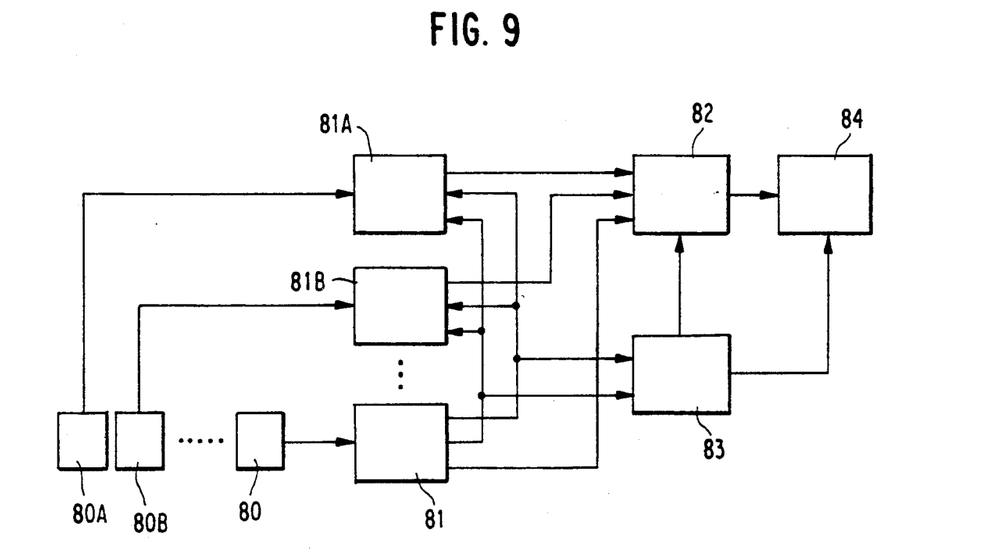
FIG. 9 is a diagram of an alternative embodiment of the optical inspection system which uses an array of 12 separate CCD cameras to image the surface directly.
Figure 10A:
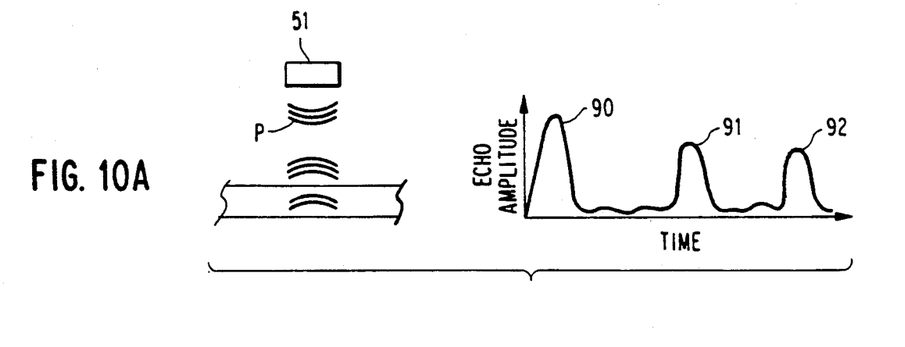
FIG. 10. illustrates the echo signals to be expected for an intact wall section, a section containing an inclusion or crack, a section corroded from the outside, and a section corroded from the inside.
Figure 10B:
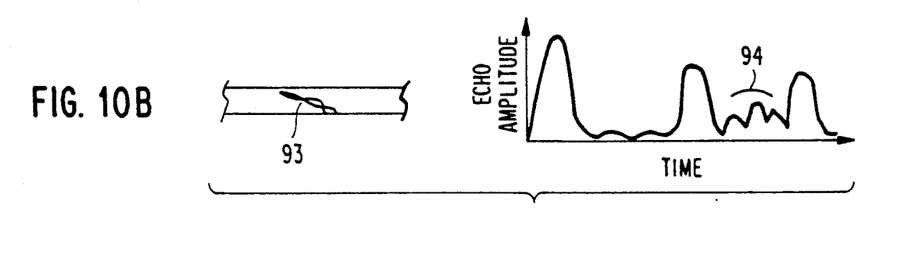
Figure 10C:
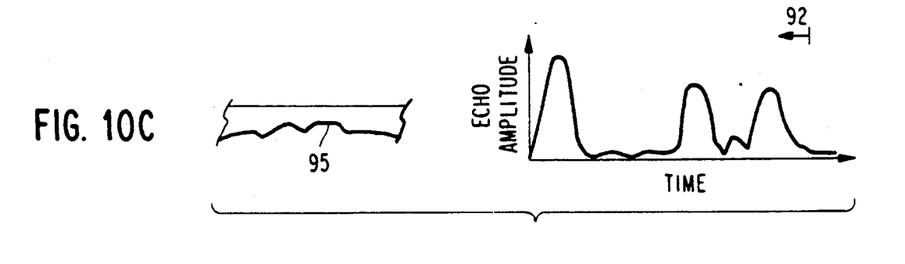
Figure 10D:
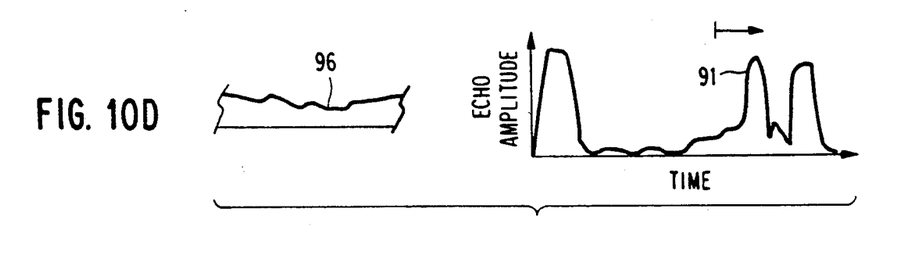

An alternative embodiment of the optical system is illustrated in FIG. 9. Twelve low resolution ($64\times 64$ pixel) CCD cameras 80 are arranged as illustrated for the fiber optic/lens case in FIGS. 8A and 8B. Here, however, CCD cameras directly image the surface rather than depending on the fiber optic/lens arrangement of the embodiment described above. The output of each camera is sent to a corresponding sample & hold circuit 81. The sample & hold outputs are then sequentially transferred to an appropriate location in the video memory 82. For example, a 30 frame per second image would require a clock 83, operating at 1.62 MHz ($30\times 64\times 64\times 12+10\%$ for overhead), to trigger the transfer of the sample & hold outputs.

The video image can be processed by conventional techniques, such as contrast enhancement, edge detection, or pixel averaging, and stored for later review. The video system may also be used in conjunction with a mouse, allowing the operator to mark the location of a surface feature and store it for future reference.

Illumination for video inspection is provided by a single high intensity bulb projected into a fiber-optic bundle which carries the light between the optics electronics 53 and the optical sensors 52. One illumination fiber-optic is provided for each optical sensor 52. Illumination is preferably provided at an angle with respect to the surface normal, to enhance contrast and visibility of surface defects.

Not all defects can be detected by an optical inspection system, even under the best of circumstances. Such defects include grain boundary corrosion, cracks, inclusions, and decreased material thickness due to erosion from below the tank bottom. However, these defects may be detected using existing ultrasonic inspection techniques. In addition, an ultrasonic inspection system may be used to confirm the results obtained with an optical system.

The applicable ultrasonic technique is illustrated in FIG. 10. An ultrasonic transducer 51 emits a pulse P and detects the echoes created when the pulse is reflected from various surfaces. The time interval between detection of the echoes indicates the distances separating the reflecting surfaces. Thus, FIG. 10A shows the echo response from a fully intact reservoir wall. A single outgoing pulse 90 gives rise to two reflected pulses, one from the near, inner wall 91 and one from the far, outer wall 92. The time interval between the detected echoes multiplied by the pulse propagation velocity in the wall material is equal to the wall thickness. The case where a defect is present within the wall is illustrated in FIG. 10B. There, the internal crack 93 provides additional reflecting surfaces and, consequently, additional echoes 94 are detected between the echoes corresponding to reflections from the near (inner) wall 91 and the far (outer) wall 92. FIG. 10C and 10D illustrate the echo patterns to be expected from a wall that has been corroded on its exterior 95 and interior 96 surfaces, respectively.

Figure 11A:
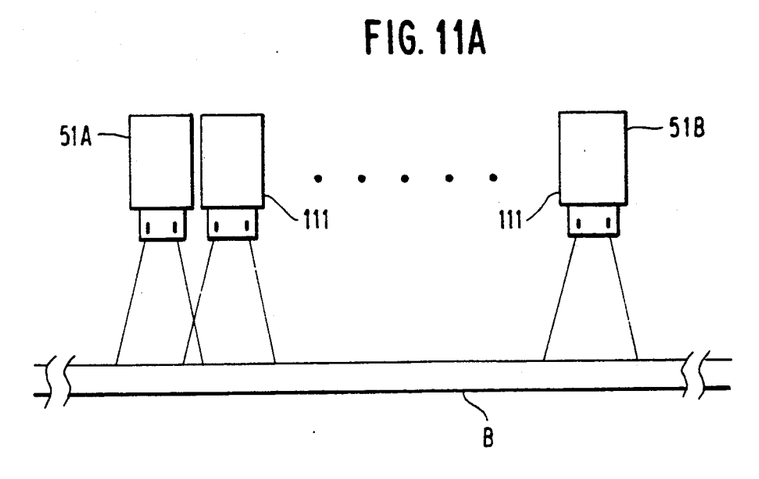
FIG. 11A. is a view of the transducer array for doing acoustic inspections.
Figure 11B:
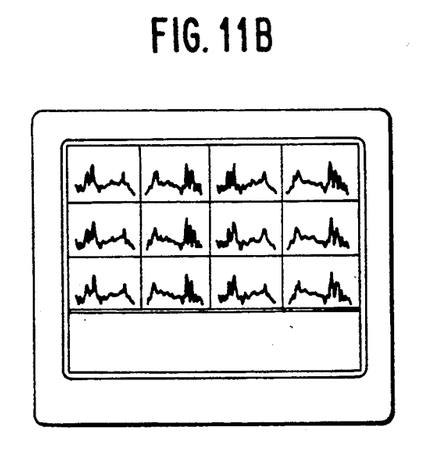
FIG. 11B. represents one mode of displaying the signals from the transducers on a video monitor.

One embodiment of the acoustic detection system is illustrated in FIG. 11A. The geometry of the system parallels that of the optical system to facilitate a comparison of the optical and acoustic images of a surface region. In the illustrated embodiment, the system consists of a linear array of twelve ultrasonic transducers 51. Baffles 111 on each transducer 51 are used to image a 1.5" diameter area of the surface, B. At a transducer separation of 1" and with the array oriented perpendicular to the direction of travel, this arrangement provides sufficient overlap to cover a 1" by 12" swath of surface. The transducers may be triggered sequentially and their outputs displayed in twelve separate amplitude-time segments on a video monitor, as illustrated in FIG. 11B. In this way, a 12"×1" swath of surface, comparable to that imaged by the lens array shown in FIGS. 7 and 8, may be acoustically imaged for analysis. The transducer characteristics are determined by the resolution necessary to detect defect features. Thus, a wavelength of 0.0156" (1/64") provides sufficient resolution to detect features of comparable size. Assuming a transmission velocity of 20,000 ft./s in steel, this wavelength corresponds to a transducer frequency of 15.4 MHz. At 100 MHz bandwidth, the signal rise time is 10.6 nanoseconds, which is reasonable relative to the 0.53 microseconds necessary to produce an 8 cycle pulse. The roundtrip travel time of a pulse is approximately 76 microseconds, assuming a 1" thick steel tank. The transducers can therefore be triggered by 0.1 Msec clock. A complete sweep of the twelve transducer array requires approximately 1.2 Msec. At 4"/s velocity, the propulsion system moves only 0.005" in the time necessary for a single sweep, leading to negligible skewing.

The external positioning system of the present invention may be either an acoustic or optical triangulation system. It is provided so that defects observed with the acoustic or optical inspection systems may be located precisely within the reservoir. In addition, the present invention may be used in a variety of situations where visual positioning of the submersible vehicle may not be possible using either the navigation camera or direct observation. The navigation system provides an alternative means for following the vehicles motion across the reservoir surface.

It should be understood that the foregoing disclosure relates only to a preferred embodiment of the invention. The present invention is intended to cover all changes and modifications which fall within the spirit and scope of the invention.

I claim:

1. An apparatus for the preparation and inspection of a submerged surface of a fluid reservoir, said apparatus comprising:
   means for moving the apparatus within a fluid in a direction of travel over an area of the submerged surface to be inspected;
   cleaning means for preparing said area for inspection comprising means for removing deposited sediment from the submerged surface and means for irrigating the cleaned surface with a stream of clean fluid; and
   inspection means for examining said prepared surface through said clean fluid.

2. The surface preparation and inspection apparatus of claim 1 further comprising movement and inspection control means, said control means being responsive to at least one of pre-programmed control and direct control from a remote location.

3. The surface preparation and inspection apparatus of claim 2 wherein said means for removing deposited sediment comprises means for sucking fluid containing suspended sediment, means for filtering said fluid to produce clean fluid and means for providing said clean fluid to said irrigating means.

4. The surface preparation and inspection apparatus of claim 2 wherein said inspection means is operatively disposed immediately after said cleaning means along said direction of travel.

5. An apparatus for preparing and inspecting the submerged surface of a fluid reservoir, said apparatus comprising:
   a chassis means, sized and shaped to provide an optimally low center of gravity and defining at least a front and an underside of said apparatus;
   propulsion means operative to provide movement to said apparatus and being mounted on said chassis means, said propulsion means comprising two independently controllable motor and track means;
   a scrubbing/vacuuming compartment disposed at said front, underside of said chassis means and comprising:
      scrubbing means designed to mechanically break up sediment on the surface beneath said apparatus; and
      vacuuming means to remove sediment and sediment-containing fluid from beneath said apparatus, resulting in a freshly cleaned surface; and
   inspection means located immediately behind the scrubbing/vacuuming means with respect to the direction of apparatus travel and operative to inspect said freshly cleaned surface.

6. An apparatus for preparing and inspecting a submerged reservoir surface as claimed in claim 5 further comprising a filtering system communicating with said scrubbing/vacuuming compartment and operative to filter sediment from fluid, said filtering system comprising:
   means to remove fluid and suspended sediment from the scrubbing/vacuuming compartment;
   means to filter the sediment from the reservoir fluid and return clean fluid to the reservoir proximate to said inspection means.

7. An apparatus for preparing and inspecting a submerged reservoir surface as claimed in claim 5 wherein said apparatus is operated from a remote control command center, said apparatus further comprising command receiving means for receiving operational commands and controlling at least one means comprised in said apparatus.

8. An apparatus for preparing and inspecting a submerged reservoir surface as claimed in claim 5 wherein said inspection means comprises:
   means to continually irrigate said freshly cleaned surface by flowing clear fluid into the volume between the inspection means and said freshly cleaned surface; and
   at least one of optical sensors and ultrasonic sensors operative to image a portion of said freshly cleaned surface.

9. An apparatus claimed in claim 8 wherein said optical and ultrasonic sensors comprise arrays generally disposed perpendicular to the direction of apparatus travel and oriented to image a surface section of width comparable to said chassis width.

10. An apparatus claimed in claim 9 wherein said scrubbing means comprises a rotating cylindrical brush disposed in said scrubbing/vacuuming compartment.

11. An apparatus claimed in claim 10 wherein said scrubbing means comprises a nozzle means, disposed in the scrubbing/vacuuming compartment and aimed at the surface beneath the apparatus, to provide at least one high velocity jet of fluid.

12. An apparatus claimed in claim 6 wherein said chassis means comprises a first and a second chassis joined by an articulated connection, said inspection means being disposed on said second chassis and said scrubbling/vacuuming department being disposed on said first chassis.

13. A method for preparing and inspecting a fluid reservoir surface coated with sediment comprising:

scrubbing a section of said surface to loosen said sediment and removing the loosened sediment to prepare a freshly cleaned surface;

interposing a clean fluid flow between said freshly cleaned surface and an inspection means; and inspecting said surface through said clean fluid flow with said inspection means.

14. The method for preparing and inspecting a fluid reservoir surface claimed in claim 13 wherein the fluid containing loosened sediment is removed from the reservoir, filtered, and returned as said clean fluid flow.

15. The method of claim 13 wherein said scrubbing step is performed by at least one of mechanical brushing and fluid sprayering.

16. The method of claim 13 wherein said step of inspecting is performed by at least one of optical inspection and acoustic inspection.

* * * * *